United States Patent [19]

Vedres et al.

[11] Patent Number: 4,780,537
[45] Date of Patent: Oct. 25, 1988

[54] PYRIMIDINE DERIVATIVES AND PROCESS PREPARING THE SAME

[75] Inventors: András Vedres; Csaba Szántay; Béla Stefkó; János Kreidl; András Nemes; Gábor Blaskó; Erik Bogsch; Dénes Máthé, all of Budapest; István Hegedüs, Balogh; Adrien Szuchovszky née Gergely, Budapest; Tamás Mester, Borsó, all of Hungary

[73] Assignee: Richter Gedeon Vegyeszeti Gyar R. T., Budapest, Hungary

[21] Appl. No.: 72,010

[22] Filed: Jul. 10, 1987

[30] Foreign Application Priority Data

Oct. 7, 1986 [HU] Hungary ............................. 2856/86

[51] Int. Cl.⁴ ........................................... C07D 239/02
[52] U.S. Cl. .................................. 544/320; 544/321; 544/323
[58] Field of Search ....................... 544/320, 321, 323; 260/691

[56] References Cited

U.S. PATENT DOCUMENTS 3,493,574  2/1970  Baranyovits et al. ............... 544/320
4,150,131  4/1979  Muller et al. ....................... 544/323

OTHER PUBLICATIONS

Mar., *Advanced Organic Chemistry*, 1970, p. 336.
*Organic Syntheses*, Collective vol. 4, pp. 5 and 42.

*Primary Examiner*—Mary C. Lee
*Assistant Examiner*—Zinna Northington
*Attorney, Agent, or Firm*—Keil & Weinkauf

[57] ABSTRACT

A pyrimidine derivative of the formulae (Ia), (Ib) and (Ic),

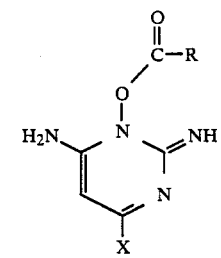

(Ia)

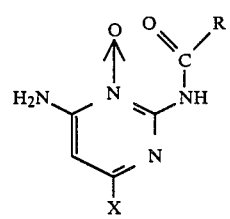

(Ib)

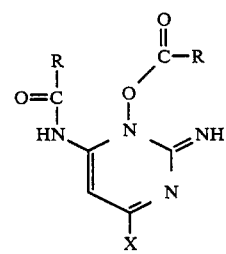

(Ic)

wherein
R stands for an alkyl group group with 1 to 6 carbon atoms or an aryl group optionally substituted by halogen atom; and
X stands for chlorine or bromine atom or an arylsulfonyloxy group optionally substituted by 1 to 3 lower alkyl groups.

The subject pyrimidine derivatives are intermediates for preparing 6-amino-1,2-dihydro-1-hydroxy-2-imino-4-piperidinopyrimidine.

9 Claims, No Drawings

PYRIMIDINE DERIVATIVES AND PROCESS PREPARING THE SAME

The invention relates to new pyrimidine derivatives of the general formulae (Ia), (Ib) and (Ic),

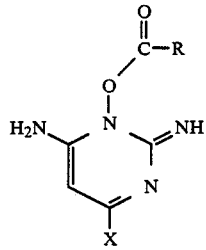
(Ia)

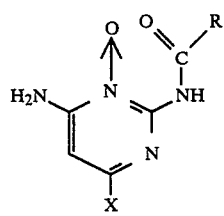
(Ib)

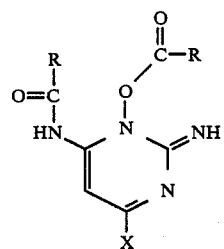
(Ic)

wherein
R stands for an alkyl group with 1 to 6 carbon atoms or an aryl group optionally substituted by halogen atom; and
X stands for chlorine or bromine atom or an arylsulfonyloxy group optionally having one or more substituents.

The invention relates further to the preparation of the novel pyrimidine derivatives of the general formulae (Ia), (Ib) and (Ic) as well as of the known pyrimidine derivatives of the general formula (Id),

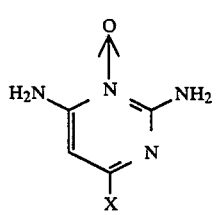
(Id)

wherein the meaning of X is the same as above.

According to the invention pure compounds of the general formulae (Ia) to (Id) and their mixtures, respectively, are prepared by reacting a 2,6-diaminopyrimidine derivative of the general formula (II)

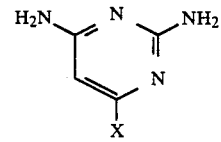
(II)

—wherein the meaning of X is the same as above—with an acid anhydride of the general formula (III)

$$\underset{R}{\overset{R}{\underset{\parallel}{C}}}\underset{O}{\overset{O}{\underset{\parallel}{C}}}$$ (III)

—wherein the meaning of R is the same as above—in the presence of water and hydrogen peroxide and the obtained product mixture or the pure compounds of the general formulae (Ia), (Ib), (Ic) and (Id), respectively, are separated.

The new compounds of the general formulae (Ia), (Ib) and (Ic) and the known compounds of the general formula (Id) are valuable intermediates for preparing 6-amino-1,2-dihydro-1-hydroxy-2-imino-4-piperidinopyrimidine (minoxidil) exhibiting blood pressure decreasing and hair growth stimulating effects.

According to the process of the invention the compounds of the general formulae (Ia) to (Id) are prepared starting from 2,6-diaminopyrimidine derivatives of the general formula (II) (in the formulae the meaning of R and X is the same as above). The compounds of the general formula (II) are already known, e.g. those which contain chlorine or bromine atom in place of X are described in the U.S. Pat. No. 3,644,364 and those containing arylsulfonyloxy group in the place of X are disclosed in the Hungarian patent specification No. 177,601.

The compounds of the general formula (Id) wherein X stands for chlorine or bromine atom are known from the above-mentioned U.S. Pat. No. 3,644,364 and those wherein X stands for arylsulfonyloxy group are known from the Hungarian patent specification No. 177,601. The other compounds, i.e. the compounds of the general formulae (Ia) to (Ic) which can be prepared by the process of the invention are new.

The term arylsulfonyloxy group optionally having one or more substituents in the definition of substituent X in the general formulae (Ia) to (Id) and (II) preferably means a phenyl-sulfonyloxy group substituted on the phenyl ring by 1 to 3 lower alkyl groups, preferably methyl groups. Preferred representatives of such groups are the tosyloxy group and the mesitylene-sulfonyloxy group. X stands most preferably for chlorine atom.

In the general formulae (Ia) to (Id) and (III) the substituent R as an alkyl group with 1 to 6 carbon atoms can mean any saturated linear or branched chain hydrocarbyl group with 1 to 6 carbon atoms, e.g. methyl, ethyl, n- and isopropyl, n-, sec- and tert-butyl, n- and isopentyl or n- and isohexyl group, preferably an alkyl group with 1 to 4 carbon atoms, most preferably methyl group. The aryl group included also in the meaning of R can be any aryl group with 6 to 12 carbon atoms, preferably phenyl group, which may be substituted by one or more halogen atoms, preferably chlorine atom.

The invention aims at preparing compounds starting from easily available, simple chemicals and with a high yield, respectively, from which minoxidil, an active ingredient of medicine compositions, can be easily prepared with essentially higher yields than so far.

According to the patent specifications cited above the known compounds of the general formula (Id) are prepared by oxidizing the corresponding 2,6-diaminopyrimidine derivatives of the general formula (II) with m-chlorine-perbenzoic acid, in case of 4-chlorine compounds with a yield of 44% and in case of 4-tosyl compounds with a yield of 55%. Beside the low yields the known processes have further disadvantages such as the high volume demand and not lastly the fact that the oxidizing agent is a labile compound which is difficult to handle and not easily available.

Now it has been found that the above disadvantages are eliminated if the compounds of the general formula (II) are reacted in the presence of hydrogen peroxide with a proper acid anhydride of the general formula (III), instead of reacting with m-chlorine-perbenzoic acid, and beside the compounds of the general formula (Id) also further derivatives of the general formulae (Ia), (Ib) and (Ic) are obtained, through which the 6-amino-1,2-dihydro-1-hydroxy-2-imino-4-piperidinopyrimidine having therapeutical effect can be prepared essentially more preferably than with syntheses known so far.

According to the invention one proceeds preferably by dissolving the starting material of the general formula (II) (wherein the meaning of X is the same as above) together with the hydrogen peroxide, containing water of necessary volume and changing amount, in a solvent which is indifferent regarding the oxidation reaction, e.g. in alcohols, ethers, esters or ketone-type solvents, then adding the proper acid anhydride of the general formula (III) (wherein R has the above meaning) to the solution at a temperature between 40° C. and 90° C. In the course of the process, from the two reagents percarboxylic acid is obtained which oxidizes the starting material of the general formula (II). The oxidation results in forming N-oxide derivatives of the general formulae (Ia) to (Id).

The compounds of the general formulae (Ia) and (Ib) are monoacyl derivatives, with the difference that in the first group of derivatives the acyl group is on the oxygen atom bound to the nitrogen atom in position 1, in the second group of derivatives it is on the amino group of position 2. The N-acyl derivatives of the general formula (Ib) are transformed to O-acyl-derivatives of the general formula (Ia) even under extreme mild circumstances, already while dissolving or under the effect of slight heating or traces of acid-base or water. The N-oxide derivative of the general formula (Ic) is a diacyl compound in which one of the acyl groups is connected to the oxygen atom bound to the nitrogen atom in position 1, and the other is connected to the amino group in position 6. As mentioned above, the N-oxide derivative of the general formula (Id) is a known compound, which is formed quite easily from the above N-oxides of the general formulae (Ia) to (Ic) under slight alkaline effect. Inversely, the compounds of the general formulae (Ia) to (Ic) are formed from the compounds of the general formulae (Id) under the effect of slight treatment with an acid anhydride.

In the course of the practical implementation of the process the ratio of the products of the general formulae (Ia) to (Id) is the function of experimental circumstances. The product ratio is influenced primarily by the method for processing the reaction mixture, the quality of the solvent and the molar ratio of the used reagents.

If the reaction mixture is worked up after the reaction by the aid of aqueous alkaline treatment, the primarily formed acyl-compounds of the general formulae (Ia) to (Ic) are quantitatively transformed into compounds of the general formula (Id), and only this latter compound can be isolated. If in the course of processing the reaction mixture it is not subjected to such treatment, the compounds of the general formulae (Ia) to (Ic) are obtained and they can be isolated. One can proceed also in such a way that firstly the crystallized part of the compounds of the general formula (Ia) to (Id) is separated, then, after alkalizing, the obtained compound of the general formula (Id) is isolated from the mother liquor.

The process according to the invention shows a special dependence on the solvent. The pyrimidine derivative of the general formula (II) used as starting material hardly dissolves in most organic solvents. It was surprisingly found, however, that the compound of the general formula (II) dissolves under the effect of slight heating in the presence of water [2 to 20 moles of water related to 1 mole of compound (II)] in the most organic solvents, whereby its reaction gets possible. In the course of carrying out the process the water needed for the dissolution is added to the reaction mixture preferably together with the hydrogen peroxide. The product ratio of the oxidations performed under identical circumstances but different solvents is strongly different. If X stands for chlorine or bromine atom, in ethanol a mixture of the compounds of the general formulae (Ia) and (Ib) separates, whereas in tetrahydrofuran practically pure O-acyl compound of the general formula (Ia) can be prepared. However, in tert-butanol or ethyl acetate a prevailing amount of the compound of the general formula (Ia) together with a minor amount of the general formula (Ic) are obtained. If X stands for tosyl group, the compound of the general formula (Ia) is formed in ethanol and no compound of the general formula (Ib) can be isolated at all.

By increasing the amount of acid anhydride used for reaction in the same solvent, predominantly the diacyl compound of the general formula (Ic) is obtained, surprisingly even in the case when the reaction is performed in an aqueous medium. The quality of group R does not influence the product ratio.

As it was mentioned above, the common disadvantages of the known processes for the preparation of the known compounds of general formula (Id) and of other analogous compounds are the relatively low yield, the high volume demand and the labile character of the applied oxidating agent. The process of the invention is free from these disadvantages. The yields are higher, the oxidating agent itself is easily available, it is formed from simple chemicals during the reaction, and the volume demand is essentially lower than in the case of the known processes.

The 6-amino-1,2-dihydro-1-hydroxy-2-imino-4-piperidinopyridimine (minoxidil) exhibiting antihypertensive effect can be prepared from the partly new compounds according to the invention with an essentially higher yield than with the aid of the known processes. The transformation of the compounds to be prepared by the process of the invention into minoxidil is carried out by reactng them with piperidine and hydrolysing the obtained compound in the way as disclosed in the simultaneously filed Hungarian patent application No. 2855/86. Whereas the best one from the known processes according to the Hungarian patent specification No. 177,601 has only a total yield of about 20–21%, with the aid of the process of the invention minoxidil can be obtained with a total yield of about 49–50% related to the starting material of the general formula (II). In relation to the prior art processes this can be evaluated as an essential and unexpected improvement. A possible reason for the higher yields obtainable by the process of the invention is that the oxidating agent concurrently forms also protective acyl groups of the sensitive substituents of the compound to be produced. This phenomenon provides protection for the molecules against excessive oxidation.

Further details of the invention are explained by the following non-limiting Examples.

EXAMPLE 1

Preparation of 2-acetamido-4-chloro-6-aminopyrmidine-1-oxide and 6-amino-1,2-dihydro-1-acetoxy-2-imino-4-chloropyrimidine 5.0 g (0.035 mole) of 2,6-diamino-4-chloropyrimidine are dissolved in 70 ml of anhydrous ethyl alcohol. 7 ml of a 70% aqueous hydrogen peroxide solution and 14 ml of acetic anhydride are dropped into it while stirring at a temperature of 40° C. in half an hour. The mixture is stirred at 60° C. for further two hours, then it is cooled and the flaky crystals are filtered out, washed with ethanol and dried. Thus 2.67 g (38%) of 2-acetamido-4-chloro-6-aminopyrimidine-1-oxide are obtained.

IR $(cm^{-1})$ (KBr): 3400, 1690, 1640, 1610.

The mother liquor is evaporated in vacuo, 20 ml of water are added to the residue and the mixture is kept in a refrigerator for a night. The crystals are filtered, washed with water and dried. Thus 1.7 g (24%) of 6-amino-1,2-dihydro-1-acetoxy-2-imino-4-chloropyrimidine are obtained.

IR $(cm^{-1})$ (KBr): 3420, 1730, 1660, 1570, 1550.
UV (nm) (EtOH): 247, 276, 325.
NMR $(CDCl_3 + TFA\text{-}d)$ δ: 2.47 (s, 3H), 7.98 (s, 1H).

EXAMPLE 2

Preparation of 6-amino-1,2-dihydro-1-acetoxy-2-imino-4-chloropyrimidine 5 g (0.035 mole) of 2,6-diamino-4-chloropyrimidine are dissolved in 50 ml of anhydrous tetrahydrofuran. 7 ml of a 70% aqueous hydrogen peroxide solution and 16 ml of acetic anhydride are added dropwise while stirring at a temperature of 40° C. in half an hour. The mixture is stirred at 60° C. for further two hours. After evaporating the tetrahydrofuran 50 ml of water are added to the residue, then it is kept in a refrigerator for a night. Thus 4.00 g (57%) of the aimed compound separate. Further 0.77 g (11%) of this compound is obtained by filtering the product achieved by the second separation.

IR, UV and NMR spectra of the product correspond to those of the identical product in the previous Example.

EXAMPLE 3

Preparation of 6-acetamido-1,2-dihydro-1-acetoxy-2-imino-4-chlropyrimidine and 6-amino-1,2-dihydro-1-acetoxy-2-imino-4-chloropyrimidine 170 ml of tert-butanol are mixed with 17.28 g (0.12 mole) of 2,6-diamino-4-chloropyrimidine while stirring at a temperature of 50° C., then 17 ml of 30% aqueous hydrogen peroxide are added. 36 ml of acetic anhydride are dropped to the obtained solution at a temperature of 55° to 60° C. in an hour. The mixture is stirred at this temperature for a further hour, then it is cooled to 15° C. and allowed to stand for two hours. The separated crystals are filtered out, washed twice with 20 ml of water each and twice with 20 ml of ethanol each, then dried.

Thus 15 g (62%) of the aimed product consisting of 30% of the above diacetyl and 70% of the above monoacetil compound are obtained. 6 g of sodium pyrosulfite dissolved in 12 ml of water and then 170 ml of water are added to the mother liquor and it is stirred at room temperature for half an hour. Then it is distilled in vacuo to the half of its volume and neutralized with a 40% aqueous sodium hydroxide solution to pH 6. The mixture is allowed to stand in refrigerator for a night, then it is filtered, washed three times with 20 ml of water each and then dried. In this way 2.4 g (10%) of the aimed monoacetyl compound are obtained.

The data of IR, UV and NMR spectra of the monoacetyl compound correspond to those given in Example 1.

Characteristics of the aimed diacetyl compound: IR $(cm^{-1})$ (KBr): 1720, 1690, 1600, 1570.

EXAMPLE 4

Preparation of 6-acetamido-1,2-dihydro-1-acetoxy-2-imino-4-chloropyrimidine 3.2 g (0.02 mole) of 6-amino-1,2-dihydro-1-hydroxy-2-imino-4-chloropyrimidine are stirred with 30 ml of acetic anhydride at room temperature for one hour, then 200 ml of ether are added to the mixture. The obtained white crystals are filtered, washed with ether and dried.

Thus 3.9 g (80%) of the aimed compound are obtained. The physical parameters of the product correspond to those as given in Example 3.

EXAMPLE 5

Preparation of 6-amino-1,2-dihydro-1-hydroxy-2-imino-4-chloropyrimidine 1.5 g (10 mmoles) of 2,6-diamino-4-chloropyrimidine are dissolved in 20 ml of anhydrous tetrahydrofuran. A mixture of 10 ml of acetic acid and 2 ml of a 70% aqueous hydrogen peroxide solution is added in 30 minutes under stirring and reflux. The reaction mixture is boiled for four hours, evaporated in vacuo to third of its volume, and a 40% aqueous sodium hydroxide solution is added to the residue until reaching a pH value of 8. The mixture is allowed to stand in refrigerator for a night. The crystals are filtered, washed with water and dried. In this way 1.0 g (63%) of the aimed compound is obtained.

IR (cm⁻¹) (KBr): 3400, 3310, 1660, 1630.
UV (nm) (MeOH) $\lambda_{max}$: 230, 294.

EXAMPLE 6

Preparation of
6-amino-1,2-dihydro-1-acetoxy-2-imino-4-chloropyrimidine and
6-acetamido-1,2-dihydro-1-acetoxy-2-imino-4-chloropyrimidine 4.32 g (0.03 mole) of 2,6-diamino-4-chloropyrimidine and 9.3 ml of a 30% aqueous hydrogen peroxide solution are dissolved in 150 ml of water at 60° C. While mixing 18 ml of acetic anhydride are dropped to the solution at 55° to 60° C. in 40 minutes. The reaction mixture is stirred at this temperature for further one hour and a half, then cooled to 15° C. After two hours the precipitate is filtered out, washed with water and dried.

Thus 1.45 g (20%) of the aimed 6-acetamido-1,2-dihydro-1-acetoxy-2-imino-4-chloropyrimidine are obtained.

The mother liquor is neutralized with a 40% aqueous sodium hydroxide solution to pH 6 and it is allowed to stand in a refrigerator for a night. The formed crystals are filtrated, washed with water and dried. In this way 1.2 g (20%) of 6-amino-1,2-dihydro-1-acetoxy-2-imino-4-chloropyrimidine are obtained.

The physical parameters of the obtained products are the same as those of the corresponding products in Examples 1 and 3.

EXAMPLE 7

Preparation of
6-acetamido-1,2-dihydro-1-acetoxy-2-imino-4-p-toluenesulfonyloxy-pyrimidine 84 g (0.3 mole) of 2,6-diamino-4-tosyloxypyrimidine are added to 1200 ml of anhydrous tetrahydrofuran. 40 ml of a 70% aqueous hydrogen peroxide solution are dropped to the obtained suspension at room temperature while stirring, whereupon the material is dissolved. While stirring 200 ml of acetic anhydride are added to the solution at 40° C. in an hour. After adding the mixture is stirred at 60° C. for further two hours. Then the solvent is evaporated in vacuo and the residue is allowed to stand in a refrigerator for a night. The separated material is filtered, washed with tetrahydrofuran and dried. In this way 77 g (68%) of the aimed compound are obtained.

Melting point: 196° to 200° C.
IR (cm⁻¹) (KBr): 1720, 1690, 1600, 1580, 1500.
UV (nm) (EtOH) $\lambda_{max}$: 252, 285, 321.
NMR (CDCl₃+TFA-d): 2.38 (s, 3H); 2.48 (s, 3H); 2.55 (s, 3H); 7.42 (s, 1H); 7.46 and 7.98 (dd, 4H).

EXAMPLE 8

Preparation of
6-amino-1,2-dihydro-1-acetoxy-2-imino-4-p-toluenesulfonyloxy-pyrimidine 2.8 g (0.001 mole) of 2,6-diamino-4-tosyloxypyrimidine are added to 70 ml of absolute ethanol. 5 ml of a 70% aqueous hydrogen peroxide solution are added to the obtained suspension at 40° C., then 3 ml of acetic anhydride are added dropwise. The suspension is homogenised by heating to 60° C., and the solution gets slowly opalescent while standing. Tracing the reaction by thin layer chromatography it will be found that the reaction has completed and the aimed compound is accompanied by some diacetyl compound. By filtering the reaction mixture 0.35 g of a solid material is separated. If the ethyl alcohol is distilled off and the residue is allowed to stand in a refrigerator, no product separation can be observed. Of decanting the water and dissolving the residue in ethanol a crystalline product is obtained. In this way 1.95 g (54%) of the aimed compound are obtained.

IR (cm⁻¹) (KBr): 3440, 1720, 1560, 1660, 1600.
UV (nm) (EtOH) $\lambda_{max}$: 244, 260 sh, 322.
NMR (CDCl₃+TFA-d) δ: 2.44 (s, 3H), 3.50 (s, 3H), 7.53 (s, 1H), 7.48 and 8.00 (dd, 4H).

EXAMPLE 9

Preparation of
6-amino-1,2-dihydro-1-propionyloxy-2-imino-4-chloropyrimidine 8.54 g (0.06 mole) of 2,6-diamino-4-chloropyrimidine are dissolved at 40° C. in the mixture of 80 ml of tert.-butanol and 5.3 ml of a 70% aqueous hydrogen peroxide solution, then the temperature is increased to 60° C. 18 ml of propionic acid are dropped to the reaction mixture while stirring in such a way that the temperature be kept at 60±2° C. Thereafter the reaction mixture is stirred at this temperature for two hours, then it is cooled to room temperature. After two hours the separeted product is filtered, washed with ethanol and then dried.

6.34 g (49%) of 6-amino-1,2-dihydro-1-propionyloxy-2-imino-4-chloropyrimidine are obtained. After standing for a night further 0.6 g (4%) of the aimed product separate from the mother liquor.

IR (cm⁻¹) (KBr): 1760 (C=O).
¹H-NMR (DMSO-d₆) δ: 1.16 (t, 3H, CH₃), 2.65 (Q, 2H, CH₂), 7.60 (s, 1H, C₅-H), 7.62 (broad, 1H, HN=).

EXAMPLE 10

Preparation of
6-amino-1,2-dihydro-1-acetoxy-2-imino-4-chloropyrimidine and
6-acetamido-1,2-dihydro-1-acetoxy-2-imino-4-chloropyrimidine 4.32 g (0.03 mole) of 2,6-diamino-4-chloropyrimidine are dissolved in the mixture of 43 ml of ethyl acetate and 3 ml of a 70% aqueous hydrogen peroxide solution. During an hour and a half 12 ml of acetic anhydride are added at 55° to 60° C. The reaction mixture is stirred at this temperature for a further half an hour, then it is cooled and allowed to stand in a refrigerator for a night. The separated crystals are filtrated out, washed with ethyl acetate and then dried. In this way 1.80 g (25%) of 6-acetamido-1,2-dihydro-1-acetoxy-2-imino-4-chloropiperidine are obtained.

The mother liquor containing ethyl acetate is extracted with 40 ml of a 10% aqueous sodium hydroxide solution and then twice with 40 ml of water each. The fraction containing ethyl acetate is evaporated to a half of its volume, the precipitate is filtered and washed with water. Thus 1.25 g (20%) of 6-amino-1,2-dihydro-1-acetoxy-2-imino-4-chloropyrimidine are obtained.

From the united alkaline and aqueous phases further 0.6 g (10%) of the aimed product separates by the next day.

EXAMPLE 11

Preparation of 6-acetamido-1-acetoxy-2-imino-4-mesitylene-sulfonyloxy-1,2-dihydropyrimidine 45.8 g (0.15 mole) of 2,4-diamino-4-mesitylenesulfonyloxy-pryimidine are suspended in 600 ml of tetrahydrofuran in a round-bottom flask of 1000 ml provided with a mixer, a reflux cooler and a dropping funnel. 20 ml (27.2 g) of a 70% aqueous hydrogen peroxide solution are added to the suspension while stirring, whereupon the material is dissolved. Then a heating of the solution on an oil bath is started and 100 ml (108.1 g, 1.06 moles) of acetic anhydride are dropped to it at 40° C. in such a way that the temperature of the mixture shall not exceed 60° C. Thereafter the reaction mixture is stirred at 60° C. for further two hours. Then the tetrahydrofuran is evaporated in vacuo on a bath of 60° C., and the residue is cooled in a refrigerator. The separated material is filtered and washed with tetrahydrofuran.

After drying 34.6 g (56.5%) of 6-acetamido-1-acetoxy-2-imino-4-mesitylene-sulfonyloxy-1,2-dihydropyrimidine are obtained in the form of a white crystalline material.

Melting point: 162°–163° C. (decomposition).

The product is chromatographically uniform.

Analysis for the formula $C_{17}H_{20}N_4O_6S$: calculated: C=49.99%, H=4.94%, N=13.72%, S=7.85% found C=49.94%, H=4.94%, N=13.95%, S=7.76%.

IR (cm$^{-1}$) (KBr): 3400, 1720, 1695, 1580, 1200, 1175, 1050.

NMR (DMF) δ: 2.10; 2.25; 2.35 (3H, s); 2.6 (6H, 2,2',6'-CH$_3$); 6.6 (1H, s, 5-H)x; 6.85 (2H, s, 3'5'-H).

What is claimed is:

1. A pyrimidine derivative of the formulae (Ia), (Ib) and (Ic),

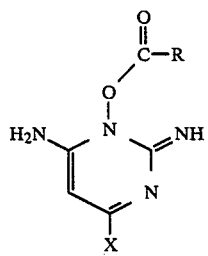 (Ia)

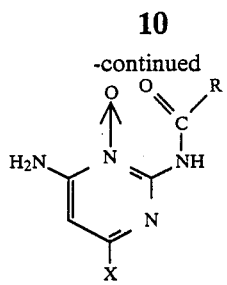 (Ib)

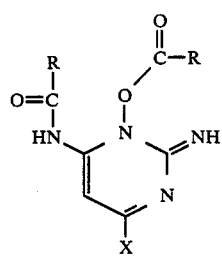 (Ic)

wherein
R stands for an alkyl group with 1 to 6 carbon atoms or an unsubstituted phenyl; or halo-substituted phenyl; and
X stands for chlorine or bromine atom or an unsubstituted phenyl-sulfonyloxy or phenylsulfonyloxy substituted by 1 to 3 lower alkyl groups.

2. A pyrimidine derivative as defined in claim 1, wherein R is CH$_3$.

3. A pyrimidine derivative as defined in claim 2, wherein X is chlorine.

4. A pyrimidine derivative as defined in claim 2, wherein X is phenylsulfonyloxy substituted by from 1 to 3 methyl groups.

5. The pyrimidine derivative of claim 1, which is 6-amino-1,2-dihydro-1-acetoxy-2-imino-4-chloropyrimidine.

6. The pyrimidine derivative of claim 1, which is 6-acetamido-1,2-dihydro-1-acetoxy-2-imino-4-chloropyrimidine.

7. The pyrimidine derivative of claim1, which is 6-acetamido-1,2-dihydro-1-acetoxy-2-imino-4-p-toluenesulfonyl-pyrimidine.

8. The pyrimidine derivative of claim 1, which is 6-amino-1,2-dihydro-1-acetoxy-2-imino-4-p-toluenesulfonyloxy-pyrimidine.

9. The pyrimidine derivative of claim 1, which is 6-acetamido-1-acetoxy-2-imino-4-mesitylene-sulfonyloxy-1,2-dihydro-pyrimidine.

* * * * *

UNITED STATES PATENT AND TRADEMARK OFFICE
CERTIFICATE OF CORRECTION

PATENT NO. : 4,780,537
DATED : October 25, 1988
INVENTOR(S) : Vedres et al.

It is certified that error appears in the above-identified patent and that said Letters Patent is hereby corrected as shown below:

Title page item [30]:

Foreign Application Priority Data (Oct. 7, 1986) should read

-- July 10, 1986 --

Signed and Sealed this

Eighteenth Day of April, 1989

Attest:

DONALD J. QUIGG

*Attesting Officer*    *Commissioner of Patents and Trademarks*